(12) United States Patent
Kemmitt et al.

(10) Patent No.: US 9,918,471 B2
(45) Date of Patent: *Mar. 20, 2018

(54) SYNERGISTIC FUNGICIDAL MIXTURES FOR FUNGAL CONTROL IN CEREALS

(71) Applicant: DOW AGROSCIENCES LLC, Indianapolis, IN (US)

(72) Inventors: Greg Kemmitt, Abingdon (GB); Olavo Correa da Silva, Carmel, IN (US); John T. Mathieson, Brownsburg, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/585,058

(22) Filed: Dec. 29, 2014

(65) Prior Publication Data

US 2015/0181870 A1    Jul. 2, 2015

Related U.S. Application Data

(60) Provisional application No. 61/922,588, filed on Dec. 31, 2013, provisional application No. 61/922,653, filed on Dec. 31, 2013.

(51) Int. Cl.
| | | |
|---|---|---|
| A01N 43/40 | (2006.01) | |
| A01N 37/50 | (2006.01) | |
| A01N 43/88 | (2006.01) | |
| A01N 43/56 | (2006.01) | |
| A01N 37/42 | (2006.01) | |

(52) U.S. Cl.
CPC ............ *A01N 43/40* (2013.01); *A01N 37/42* (2013.01)

(58) Field of Classification Search
CPC combination set(s) only.
See application file for complete search history.

(56) References Cited

U.S. PATENT DOCUMENTS

| | | | |
|---|---|---|---|
| 5,869,517 A * | 2/1999 | Muller | A01N 47/24 514/407 |
| 6,355,660 B1 | 3/2002 | Ricks | |
| 6,521,622 B1 | 2/2003 | Ricks | |
| 6,706,740 B2 | 3/2004 | Ricks | |
| 6,861,390 B2 | 3/2005 | Meyer et al. | |
| 6,927,225 B2 | 8/2005 | Ricks | |
| 7,034,035 B2 | 4/2006 | Ricks | |
| 7,183,278 B1 | 2/2007 | Imamura | |
| 7,250,389 B1 | 7/2007 | Sakanaka | |
| 8,470,840 B2 | 6/2013 | Klittich et al. | |
| 8,785,479 B2 | 7/2014 | Meyer | |
| 8,835,462 B2 | 9/2014 | Meyer | |
| 8,883,811 B2 | 11/2014 | Owen | |
| 2002/0177578 A1 | 11/2002 | Ricks | |
| 2003/0018012 A1 | 1/2003 | Ricks | |
| 2003/0018052 A1 | 1/2003 | Ricks | |
| 2003/0022902 A1 | 1/2003 | Ricks | |
| 2004/0034025 A1 | 2/2004 | Ricks | |
| 2004/0048864 A1 | 3/2004 | Ricks | |
| 2004/0171838 A1 | 9/2004 | Meyer | |
| 2004/0186296 A1 | 9/2004 | Nyaz | |
| 2004/0192924 A1 * | 9/2004 | Meyer | A01N 43/40 546/281.7 |
| 2005/0239873 A1 | 10/2005 | Hockenbery | |

(Continued)

FOREIGN PATENT DOCUMENTS

| | | |
|---|---|---|
| CN | 102210308 A | 10/2011 |
| EP | 1516874 | 3/2005 |

(Continued)

OTHER PUBLICATIONS

Webster's New World Dictionary, $2^{nd}$ college edition, The World Publishing Co., NY, 1972, p. 1127.*
Issac, S., "What is the mode of action of fungicides and how do fungi develop resistance?" Mycologist, vol. 13, Part 1, pp. 38-39 (Feb. 1999).*
Leonard, P.K., "Resistance risk evaluation, 'a European regulatory perspective," Crop Protection, vol. 19, pp. 905-909 (2000).*
Bartlett, D.W. et al., "The strobilurin fungicides," Pest Management Science, vol. 58 pp. 649-662 (2002).*
HCAPLUS abstract 2001:1405 (2001).*

(Continued)

*Primary Examiner* — John Pak
(74) *Attorney, Agent, or Firm* — Charles W. Amett; Faegre Baker Daniels LLP

(57) ABSTRACT

A fungicidal composition containing a fungicidally effective amount of a compound of Formula I:

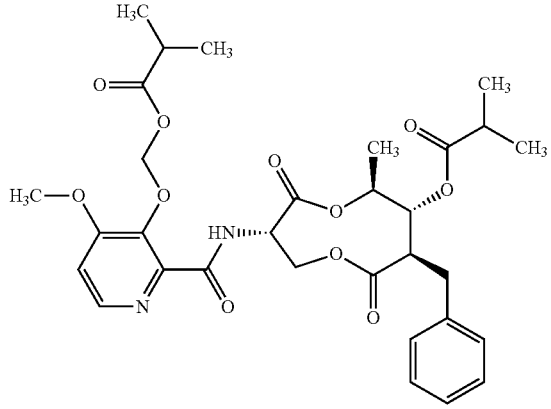

Formula I (3S,6S,7R,8R)-8-benzyl-3-(3-((isobutyryloxy)methoxy)-4-methoxypicolinamido)-6-methyl-4,9-dioxo-1,5-dioxonan-7-yl isobutyrate, and at least one fungicide selected from the group consisting of fluoxastrobin, trifloxystrobin, and picoxystrobin, provides synergistic control of selected fungi.

18 Claims, No Drawings

(56) References Cited

U.S. PATENT DOCUMENTS

| | | |
|---|---|---|
| 2007/0060579 A1 | 3/2007 | Wachendorff-Neumann |
| 2007/0066629 A1 | 3/2007 | Tormo i Blasco |
| 2009/0306142 A1 | 12/2009 | Carson |
| 2011/0053966 A1 | 3/2011 | Klittich et al. |
| 2011/0082160 A1 | 4/2011 | Owen et al. |
| 2011/0082162 A1 | 4/2011 | Lorsbach et al. |
| 2012/0157485 A1 | 6/2012 | Lorsbach et al. |
| 2013/0203708 A1 | 8/2013 | Andersch et al. |
| 2013/0296371 A1 | 11/2013 | Meyer |
| 2013/0296374 A1 | 11/2013 | Owen et al. |
| 2014/0187508 A1 | 7/2014 | Ouimette et al. |
| 2014/0187587 A1 | 7/2014 | Ouimette et al. |
| 2014/0187588 A1 | 7/2014 | Lalonde |
| 2014/0187590 A1 | 7/2014 | Ouimette et al. |
| 2014/0275171 A1 | 9/2014 | Meyer |
| 2015/0065529 A1 | 3/2015 | Owen |
| 2015/0181871 A1 | 7/2015 | Kemmett |

FOREIGN PATENT DOCUMENTS

| | | |
|---|---|---|
| WO | 2001/14339 | 3/2001 |
| WO | WO03022053 A1 | 3/2003 |
| WO | 2009040397 | 9/2008 |
| WO | WO2011048120 A1 | 4/2011 |
| WO | 2012/070015 | 5/2012 |
| WO | WO2013116251 A2 | 8/2013 |
| WO | 2014106254 A1 | 7/2014 |
| WO | 2014106259 A1 | 7/2014 |

OTHER PUBLICATIONS

International Search Report and Written Opinion dated Apr. 28, 2015 in related International Application No. PCT/US2014/072603.
International Search Report and Written Opinion dated Mar. 25, 2015 in related International Application No. PCT/US2014/072602.
Anonymous, Synergistic Fungicidal Composition of Heterocyclic Aromatic Amides and Trizaoles, ip.com, Electronic Publication, 2004, 11 pages.
Anonymous, Synergistic Fungicidal Composition of Heterocyclic Aromatic Amides and Triazoles, ip.com Journal, ip.com Inc., West Henrietta, NY, US, Dates Jul. 2004, 10 pages.
K. Tani, et al, Journal of Antibiotics, vol. 55, No. 3, Mar. 2002, pp. 315-321.
Z. Hu, et al, Synthesis of Novel Analogues of Antimycin A3, Tetrahedron Letters 49 (2008) pp. 5192-5195.
Y. Usuki, et al, Journal of Antibiotics, vol. 55, No. 6, Jun. 2002, pp. 607-610.

* cited by examiner

SYNERGISTIC FUNGICIDAL MIXTURES FOR FUNGAL CONTROL IN CEREALS

CROSS REFERENCE TO RELATED APPLICATIONS

This application claims the benefit of U.S. Provisional Patent Application Ser. Nos. 61/922,588 and 61/922,653, both filed Dec. 31, 2013, which are expressly incorporated by reference herein.

FIELD

This disclosure concerns a synergistic fungicidal composition containing (a) a compound of Formula I, (3S,6S,7R,8R)-8-benzyl-3-(3-((isobutyryloxy)methoxy)-4-methoxypicolinamido)-6-methyl-4,9-dioxo-1,5-dioxonan-7-yl isobutyrate, and (b) at least one fungicide selected from the group consisting of a strobilurin, for example pyraclostrobin, fluoxastrobin, azoxystrobin, trifloxystrobin, picoxystrobin, and kresoxim methyl, a succinate dehydrogenase-inhibitor, for example: fluxapyroxad, benzovindiflupyr, penthiopyrad, isopyrazam, bixafen, boscalid, penflufen, and fluopyram, an ergosterol biosynthesis-inhibitor, for example prothioconazole, epoxiconazole, cyproconazole, myclobutanil, prochloraz, metconazole, difenconazole, tebuconazole, tetraconazole, fenbuconazole, propiconazole, fluquinconazole, flusilazole, flutriafol, fenpropimorph, and prochloraz, and a multi-site-inhibitor, for example mancozeb and chlorothalonil, or other commercial fungicides to provide control of any plant fungal pathogen.

BACKGROUND AND SUMMARY

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield and the quality of the crop, and consequently, increase the value of the crop. In most situations, the increase in value of the crop is worth at least three times the cost of the use of the fungicide.

However, no one fungicide is useful in all situations and repeated usage of a single fungicide frequently leads to the development of resistance to that and related fungicides. Consequently, research is being conducted to produce fungicides and combinations of fungicides that are safer, that have better performance, that require lower dosages, that are easier to use, and that cost less.

Synergism occurs when the activity of two or more compounds exceeds the activities of the compounds when used alone.

It is an object of this disclosure to provide synergistic compositions comprising fungicidal compounds. It is a further object of this disclosure to provide processes that use these synergistic compositions. The synergistic compositions are capable of preventing or curing, or both, diseases caused by fungi of the classes Ascomycetes and Basidiomycetes. In addition, the synergistic compositions have improved efficacy against the Ascomycete and Basidiomycete pathogens, including leaf blotch and brown rust of wheat. In accordance with this disclosure, synergistic compositions are provided along with methods for their use.

According to an exemplary embodiment of the present disclosure, a synergistic fungicidal mixture is provided including a fungicidally effective amount of a compound of Formula I, and at least one strobilurin fungicide.

According to another exemplary embodiment of the present disclosure, a fungicidal composition is provided including a fungicidally effective amount of the fungicidal mixture and an agriculturally acceptable adjuvant or carrier.

According to yet another exemplary embodiment of the present disclosure, a method is provided for the control and prevention of fungal attack on a plant, the method including: applying a fungicidally effective amount of a compound of Formula I and at least one strobilurin fungicide, wherein said effective amount is applied to at least one of the plant, an area adjacent to the plant, soil adapted to support growth of the plant, a root of the plant, foliage of the plant, and a seed adapted to produce the plant.

According to still yet another exemplary embodiment of the present disclosure, a method is provided for the control and prevention of fungal attack on a plant, the method including: applying a fungicidally effective amount of a compound of Formula I and at least one fungicide selected from the group consisting of fluoxastrobin, trifloxystrobin, picoxystrobin, benzovindiflupyr, and penthiopyrad, wherein said effective amount is applied to at least one of the plant, an area adjacent to the plant, soil adapted to support growth of the plant, a root of the plant, foliage of the plant, and a seed adapted to produce the plant.

In certain embodiments, the at least one strobilurin is selected from the group consisting of fluoxastrobin, trifloxystrobin, and picoxystrobin.

In certain embodiments, the concentration ratio of Compound I to fluoxastrobin is between about 1:156 and about 52:1 in 1DP assays.

In certain embodiments, the concentration ratio of Compound I to fluoxastrobin is between about 1:1 and about 52:1 in 3DC assays.

In certain embodiments, the concentration ratio of Compound I to trifloxystrobin is between about 1:625 and about 52:1 in 1DP assays.

In certain embodiments, the concentration ratio of Compound I to picoxystrobin is between about 1:4 and about 1:208 in 3DC assays.

In certain embodiments, the concentration ratio of Compound I to benzovindiflupyr is between about 1:39 and about 16:1 in 1DP assays.

In certain embodiments, the concentration ratio of Compound I to benzovindiflupyr is between about 1:4 and about 1:16 in 3DC assays.

In certain embodiments, the concentration ratio of Compound I to penthiopyrad is between about 1:1 and about 4:1 in 1DP assays.

In certain embodiments, the concentration ratio of Compound I to penthiopyrad is between about 1:1 and about 52:1 in 3DC assays.

DETAILED DESCRIPTION

The present disclosure concerns a synergistic fungicidal mixture comprising an fungicidally effective amount of (a) a compound of Formula I, (3S,6S,7R,8R)-8-benzyl-3-(3-((isobutyryloxy)methoxy)-4-methoxypicolinamido)-6-methyl-4,9-dioxo-1,5-dioxonan-7-yl isobutyrate, and (b) at least one fungicide selected from the group consisting of a strobilurin, for example pyraclostrobin, fluoxastrobin, azoxystrobin, trifloxystrobin, picoxystrobin, and kresoxim methyl, a succinate dehydrogenase-inhibitor, for example fluxapyroxad, benzovindiflupyr, penthiopyrad, isopyrazam, bixafen, boscalid, penflufen, and fluopyram, an ergosterol biosynthesis-inhibitor, for example prothioconazole, epoxiconazole, cyproconazole, myclobutanil, prochloraz, metconazole, difenconazole, tebuconazole, tetraconazole, fenbuconazole, propiconazole, fluquinconazole, flusilazole, flutriafol, fenpropimorph, and prochloraz, and a multi-site-inhibitor, for example mancozeb and chlorothalonil, or other commercial fungicides to provide control of any plant fungal pathogen.

Formula I

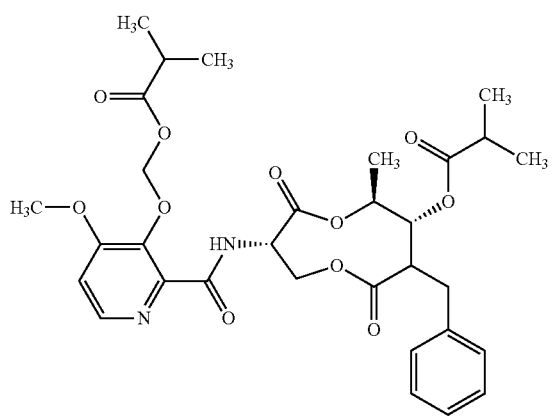

As used herein, a "fungicidally effective amount" is an amount of an active ingredient or a synergistic fungicidal mixture that causes a "fungicidal effect," i.e., kills or inhibits the plant disease for which control is desired.

As used herein, fluoxastrobin is the common name for (E)-{2-[6-2-chlorophenoxy)-5-fluoropyrimidin-4-yloxy]phenyl}(5,6-dihydro-1,4,2-dioxazin-3-yl)methanone O-methyloxime and possesses the following structure:

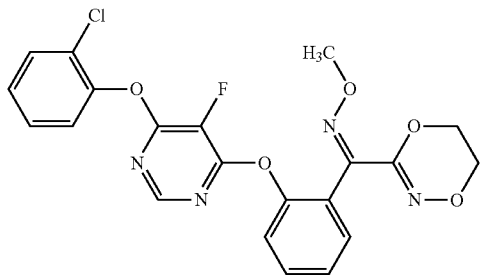 [SMILES: CO/N=C(\C1=NOCCO1)c1ccccc1Oc1ncnc(Oc2ccccc2Cl)c1F]

Its fungicidal activity is exemplified in *The e-Pesticide Manual*, Version 5.2, 2011. Exemplary uses of fluoxastrobin include, but are not limited to, use as a foliar spray in cereals for control of *Septoria* leaf spot diseases (*Septoria tritici* and *Leptosphaeria nodorum*), rusts of wheat and barley (*Puccinia recondita, P. striiformis, P. hordei*), *Helminthosporium* diseases like *Pyrenophora teres* (net blotch of barley) and *Pyrenophora tritici-repentis* (tan spot).

As used herein, trifloxystrobin is the common name for methyl (αE)-α-(methoxyimino)-2-[[[[(1E)-1-[3-(trifluoromethyl)phenyl]ethylidene]amino]oxy]methyl]-benzeneacetate and possesses the following structure:

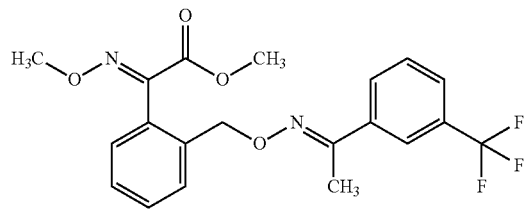 [SMILES: CO/N=C(/C(=O)OC)c1ccccc1CO/N=C(\C)c1cccc(C(F)(F)F)c1]

Its fungicidal activity is described in *The Pesticide Manual*, Fifteenth Edition, 2009. Trifloxystrobin provides broad-spectrum control of a variety of fungal pathogens on a wide variety of fruits, vegetables, and crops.

As used herein, picoxystrobin is the common name for methyl (E)-3-methoxy-2-[2-(6-trifluoromethyl-2-pyridyloxymethyl)phenyl]acrylate and possesses the following structure:

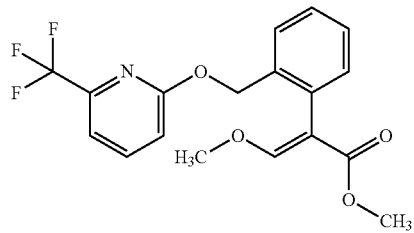 [SMILES: CO/C=C(/C(=O)OC)c1ccccc1COc1cccc(C(F)(F)F)n1]

Its fungicidal activity is described in *The e-Pesticide Manual*, Version 5.2, 2011. Exemplary uses of picoxystrobin include, but are not limited to, broad-spectrum disease control in cereals, including *Mycosphaerella graminicola, Phaeosphaeria nodorum, Puccinia recondita* (brown rust), *Helminthosporium tritici-repentis* (tan spot) and *Blumeria graminis* f.sp. *tritici* (strobilurin-sensitive powdery mildew) in wheat; *Helminthosporium teres* (net blotch), *Rhynchosporium secalis, Puccinia hordei* (brown rust) and *Erysiphe graminis* f.sp. *hordei* (strobilurin-sensitive powdery mildew) in barley; *Puccinia coronata* and *Helminthosporium avenae* in oats; and *Puccinia recondita* and *Rhynchosporium secalis* in rye.

As used herein, benzovindiflupyr is the common name for N-[(1RS,4SR)-9-(dichloromethylene)-1,2,3,4-tetrahydro-1,4-methanonaphthalen-5-yl]-3-(difluoromethyl)-1-methyl-pyrazole-4-carboxamide and possesses the following structure:

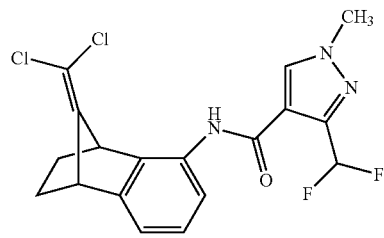 [SMILES: Cn1cc(C(=O)Nc2cccc3c2C2CCC3C2=C(Cl)Cl)c(C(F)F)n1]

Its fungicidal activity is exemplified in Agrow Intelligence (https://www.agra-net.net/agra/agrow/databases/agrow-intelligence/). Exemplary uses of benzovindiflupyr include, but are not limited to, controlling a variety of pathogens such as *Botrytis* spp., *Erysiphe* spp., *Rhizoctonia* spp., *Septoria* spp., *Phytophthora* spp., *Pythium* spp., *Phakospora pachyrhizi, and *Puccinia recondita*, in a range of crops including vines, cereals, soybeans, cotton, and fruit and vegetable crops.

As used herein, penthiopyrad is the common name for N-[2-(1,3-dimethylbutyl)-3-thienyl]-1-methyl-3-(trifluoromethyl)-1H-pyrazole-4-carboxamide and possesses the following structure:

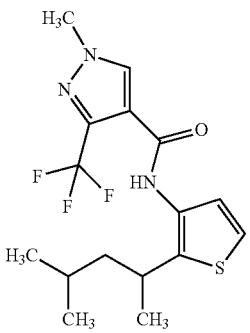 [SMILES: CC(C)CC(C)c1sccc1NC(=O)c1cn(C)nc1C(F)(F)F]

Its fungicidal activity is described in *The Pesticide Manual*, Fourteenth Edition, 2006. Penthiopyrad provides control of rust and *Rhizoctonia* diseases, as well as grey mold, powdery mildew, and apple scab.

In the compositions described herein, the concentration ratio of the compound of Formula I at which the fungicidal effect is synergistic with the other fungicides lies within the range of about 1:208 and about 52:1 in 3 Day Curative (3DC) assays and within the range of about 1:625 and about 52:1 in One Day Protectant (1DP) assays.

In one embodiment, the concentration ratio of the compound of Formula I to fluoxastrobin at which the fungicidal effect is synergistic lies within the range of between about 1:1 and about 52:1 in 3DC assays and within the range of between about 1:156 and about 52:1 in 1DP assays.

In one embodiment, the concentration ratio of the compound of Formula I to trifloxystrobin at which the fungicidal effect is synergistic lies within the range of between about 1:625 and about 52:1 in 1DP assays.

In one embodiment, the concentration ratio of the compound of Formula I to picoxystrobin at which the fungicidal effect is synergistic lies within the range of between about 1:4 and about 1:208 in 3DC assays.

In one embodiment, the concentration ratio of the compound of Formula I to benzovindiflupyr at which the fungicidal effect is synergistic lies within the range of between about 1:4 and about 1:16 in 3DC assays and within the range of between about 1:39 and about 16:1 in 1DP assays.

In one embodiment, the concentration ratio of the compound of Formula I to penthiopyrad at which the fungicidal effect is synergistic lies within the range of between about 1:1 and about 52:1 in 3DC assays and within the range of between about 1:1 and about 4:1 in 1DP assays.

The rate at which the synergistic composition is applied will depend upon the particular type of fungus to be controlled, the degree of control required, and the timing and method of application. In general, the composition of the disclosure can be applied at an application rate of between about 60 grams per hectare (g/ha) and about 850 g/ha based on the total amount of active ingredients in the composition.

The synergistic composition comprising fluoxastrobin and the compound of Formula I is applied at a rate between about 110 g/ha and about 500 g/ha. Fluoxastrobin is applied at a rate between about 75 g/ha and about 200 g/ha and the compound of Formula I is applied at a rate between about 35 g/ha and about 300 g/ha.

The synergistic composition comprising trifloxystrobin and the compound of Formula I is applied at a rate between about 85 g/ha and about 850 g/ha. Trifloxystrobin is applied at a rate between about 50 g/ha and about 550 g/ha and the compound of Formula I is applied at a rate between about 35 g/ha and about 300 g/ha.

The synergistic composition comprising picoxystrobin and the compound of Formula I is applied at a rate between about 85 g/ha and about 550 g/ha. Picoxystrobin is applied at a rate between about 50 g/ha and about 250 g/ha and the compound of Formula I is applied at a rate between about 35 g/ha and about 300 g/ha.

The synergistic composition comprising benzovindiflupyr and the compound of Formula I is applied at a rate between about 60 g/ha and about 600 g/ha. Benzovindiflupyr is applied at a rate between about 25 g/ha and about 300 g/ha and the compound of Formula I is applied at a rate between about 35 g/ha and about 300 g/ha.

The synergistic composition comprising penthiopyrad and the compound of Formula I is applied at a rate between about 135 g/ha and about 700 g/ha. Penthiopyrad is applied at a rate between about 100 g/ha and about 400 g/ha and the compound of Formula I is applied at a rate between about 35 g/ha and about 300 g/ha.

The components of the synergistic mixture of the present disclosure can be applied either separately or as part of a multipart fungicidal system.

The synergistic mixture of the present disclosure can be applied in conjunction with one or more other fungicides to control a wider variety of undesirable diseases. When used in conjunction with other fungicide(s), the presently claimed compounds may be formulated with the other fungicide(s), tank mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl) phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

The compositions of the present disclosure are preferably applied in the form of a formulation comprising a composition of (a) a compound of Formula I and (b) at least one fungicide selected from the group consisting of fluoxastrobin, trifloxystrobin, picoxystrobin, benzovindiflupyr, and penthiopyrad, together with a phytologically acceptable carrier.

Concentrated formulations can be dispersed in water, or another liquid, for application, or formulations can be dust-like or granular, which can then be applied without further treatment. The formulations are prepared according to procedures which are conventional in the agricultural chemical art, but which are novel and important because of the presence therein of a synergistic composition.

The formulations that are applied most often are aqueous suspensions or emulsions. Either such water-soluble, water-suspendable, or emulsifiable formulations are solids, usually known as wettable powders, or liquids, usually known as emulsifiable concentrates, aqueous suspensions, or suspension concentrates. The present disclosure contemplates all vehicles by which the synergistic compositions can be formulated for delivery and use as a fungicide.

As will be readily appreciated, any material to which these synergistic compositions can be added may be used, provided they yield the desired utility without significant interference with the activity of these synergistic compositions as antifungal agents.

Wettable powders, which may be compacted to form water-dispersible granules, comprise an intimate mixture of the synergistic composition, a carrier, and agriculturally acceptable surfactants. The concentration of the synergistic composition in the wettable powder is usually from about 10% to about 90% by weight, more preferably about 25% to about 75% by weight, based on the total weight of the formulation. In the preparation of wettable powder formulations, the synergistic composition can be compounded with any of the finely divided solids, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier is ground or mixed with the synergistic composition in a volatile organic solvent. Effective surfactants, comprising from about 0.5% to about 10% by weight of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the synergistic composition comprise a convenient concentration, such as from about 10% to about 50% by weight, in a suitable liquid, based on the total weight of the emulsifiable concentrate formulation. The components of the synergistic compositions, jointly or separately, are dissolved in a carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which can be employed in preparing the emulsifiable concentrates of the present disclosure are the aromatic liquids such as xylene, propyl benzene fractions, or mixed naphthalene fractions, mineral oils, substituted aromatic organic liquids such as dioctyl phthalate, kerosene, dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface-active dispersing agents are usually employed in liquid formulations and in the amount of from 0.1 to 20 percent by weight of the combined weight of the dispersing agent with the synergistic compositions. The formulations can also contain other compatible additives, for example, plant growth regulators and other biologically active compounds used in agriculture.

Aqueous suspensions comprise suspensions of one or more water-insoluble compounds, dispersed in an aqueous vehicle at a concentration in the range from about 5% to about 70% by weight, based on the total weight of the aqueous suspension formulation. Suspensions are prepared by finely grinding the components of the synergistic combination either together or separately, and vigorously mixing the ground material into a vehicle comprised of water and surfactants chosen from the same types discussed above. Other ingredients, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

The synergistic composition may also be applied as a granular formulation, which is particularly useful for applications to the soil. Granular formulations usually contain from about 0.5% to about 10% by weight of the compounds, based on the total weight of the granular formulation, dispersed in a carrier which consists entirely or in large part of coarsely divided attapulgite, bentonite, diatomite, clay or a similar inexpensive substance. Such formulations are usually prepared by dissolving the synergistic composition in a suitable solvent and applying it to a granular carrier which has been preformed to the appropriate particle size, in the range of from about 0.5 to about 3 mm. Such formulations may also be prepared by making a dough or paste of the carrier and the synergistic composition, and crushing and drying to obtain the desired granular particle.

Dusts containing the synergistic composition are prepared simply by intimately mixing the synergistic composition in powdered form with a suitable dusty agricultural carrier, such as, for example, kaolin clay, ground volcanic rock, and the like. Dusts can suitably contain from about 1% to about 10% by weight of the synergistic composition/carrier combination.

The formulations may contain agriculturally acceptable adjuvant surfactants to enhance deposition, wetting and penetration of the synergistic composition onto the target crop and organism. These adjuvant surfactants may optionally be employed as a component of the formulation or as a tank mix. The amount of adjuvant surfactant will vary from about 0.01 percent to about 1.0 percent volume/volume (v/v) based on a spray-volume of water, preferably about 0.05 to about 0.5 percent. Suitable adjuvant surfactants include ethoxylated nonyl phenols, ethoxylated synthetic or natural alcohols, salts of the esters or sulfosuccinic acids, ethoxylated organosilicones, ethoxylated fatty amines and blends of surfactants with mineral or vegetable oils.

The formulations may optionally include combinations that can comprise at least 1% by weight of one or more of the synergistic compositions with another pesticidal compound. Such additional pesticidal compounds may be fungicides, insecticides, nematocides, miticides, arthropodicides, bactericides or combinations thereof that are compatible with the synergistic compositions of the present disclosure in the medium selected for application, and not antagonistic to the activity of the present compounds. Accordingly, in such embodiments the other pesticidal compound is employed as a supplemental toxicant for the same or for a different pesticidal use. The pesticidal compound and the synergistic composition can generally be mixed together in a weight ratio of from about 1:100 to about 100:1.

The present disclosure includes within its scope methods for the control or prevention of fungal attack. These methods comprise applying to the locus of the fungus, or to a locus in which the infestation is to be prevented (for example applying to wheat or barley plants), a fungicidally effective amount of the synergistic composition. The synergistic composition is suitable for treatment of various plants at fungicidal levels, while exhibiting low phytotoxicity. The synergistic composition is useful in a protectant or eradicant fashion. The synergistic composition is applied by any of a variety of known techniques, either as the synergistic composition or as a formulation comprising the synergistic composition. For example, the synergistic compositions may be applied to the roots, seeds or foliage of plants for the control of various fungi, without damaging the commercial value of the plants. The synergistic composition is applied in the form of any of the generally used formulation types, for example, as solutions, dusts, wettable powders, flowable concentrates, or emulsifiable concentrates. These materials are conveniently applied in various known fashions.

The synergistic composition has been found to have significant fungicidal effect, particularly for agricultural use. The synergistic composition is particularly effective for use with agricultural crops and horticultural plants, or with wood, paint, leather or carpet backing.

In particular, the synergistic composition is effective in controlling a variety of undesirable fungi that infect useful plant crops. The synergistic composition may be used against a variety of Ascomycete and Basidiomycete fungi, including for example the following representative fungi species: wheat brown rust (*Puccinia recondita*; Bayer code PUCCRT); stripe rust of wheat (*Puccinia striiformis*; Bayer code PUCCST); leaf blotch of wheat (*Mycosphaerella graminicola*; anamorph: *Septoria tritici*; Bayer code SEPTTR); glume blotch of wheat (*Leptosphaeria nodorum*; Bayer code LEPTNO; anamorph: *Stagonospora nodorum*); spot blotch of barley (*Cochliobolus sativum*; Bayer code COCHSA; anamorph: *Helminthosporium sativum*); leaf spot of sugar beets (*Cercospora beticola*; Bayer code CERCBE); leaf spot of peanut (*Mycosphaerella arachidis*; Bayer code MYCOAR; anamorph: *Cercospora arachidicola*); cucumber anthracnose (*Glomerella lagenarium*; anamorph: *Colletotrichum lagenarium*; Bayer code COLLLA), and black sigatoka disease of banana (*Mycosphaerella fijiensis*; BAYER code MYCOFI). It will be understood by those in the art that the efficacy of the synergistic compositions for one or more of the foregoing fungi establishes the general utility of the synergistic compositions as fungicides.

The synergistic compositions have a broad range of efficacy as a fungicide. The exact amount of the synergistic composition to be applied is dependent not only on the relative amounts of the components, but also on the particular action desired, the fungal species to be controlled, and the stage of growth thereof, as well as the part of the plant or other product to be contacted with the synergistic composition. Thus, formulations containing the synergistic composition may not be equally effective at similar concentrations or against the same fungal species.

The synergistic compositions are effective in use with plants in a disease-inhibiting and phytologically acceptable amount. The term "disease-inhibiting and phytologically acceptable amount" refers to an amount of the synergistic composition that kills or inhibits the plant disease for which control is desired, but is not significantly toxic to the plant. The exact concentration of synergistic composition required varies with the fungal disease to be controlled, the type of formulation employed, the method of application, the particular plant species, climate conditions, and the like.

The present compositions can be applied to fungi or their locus by the use of conventional ground sprayers, granule applicators, and by other conventional means known to those skilled in the art.

The following examples are provided to further illustrate the disclosure. They are not meant to be construed as limiting the disclosure.

EXAMPLES

Evaluation of Curative Activity of Fungicide Mixtures vs. Wheat Brown Rust (*Puccinia recondita*; Bayer code: PUCCRT):

Yuma wheat seedlings were grown as described above and inoculated with an aqueous spore suspension of *Puccinia recondita* 3 days prior to (3 days curative; 3DC) and 1 day after (1 day protectant; 1DP) fungicide treatment. After inoculation, plants were kept in 100% relative humidity for 24 hours (hr) in a dark dew room to allow spores to germinate and infect plants. The plants were then transferred to a greenhouse for disease to develop.

Treatments consisted of fungicide compounds of Formula I and at least one fungicide selected from the group consisting of fluoxastrobin, trifloxystrobin, picoxystrobin, benzovindiflupyr, and penthiopyrad, either used individually or as two-way mixture with compounds I.

Spray Solution Preparation:

active ingredients were dissolved in acetone as a stock solution and serial diluted four times. Final fungicide rates were obtained by mixing the stock solution diluted with 9 parts of water containing 110 parts per million (ppm) Triton X-100.

Fungicide Application:

twenty milliliter (mL) fungicide solutions were sprayed onto 12 pots of plants using an automated booth sprayer, which utilized two 6218¼ JAUPM spray nozzles operating at 20 pounds per square inch (psi) set at opposing angles to cover both leaf surfaces. Control plants were sprayed in the same manner with the solvent blank. Plants were inoculated 24 hr after fungicide application Diseases Assessment:

infection levels were assessed visually and scored using 0 to 100 percent, 7 days after inoculation of rust. The percent disease control was calculated using the ratio of treated by untreated plants.

Colby's equation was used to determine the fungicidal effects expected from the mixtures. (See Colby, S. R. Calculation of the synergistic and antagonistic response of herbicide combinations. *Weeds* 1967, 15, 20-22.)

The following equation was used to calculate the expected activity of mixtures containing two active ingredients, A and B:

$$\text{Expected} = A + B - (A \times B/100)$$

A=observed efficacy of active component A at the same concentration as used in the mixture;

B=observed efficacy of active component B at the same concentration as used in the mixture.

Representative synergistic interactions are presented in the following Tables 1-2.

TABLE 1

Synergistic Interactions Of Compound I And Other Fungicides In 1 Day Protectant (1 DP) *Puccinia recondita* (PUCCRT) Tests.

| Composition | Rates (ppm)* | PUCCRT* (% DC)* Observed* | Expected* | Synergism Factor* |
|---|---|---|---|---|
| penthiopyrad + Cmpd. I | 1.56 + 1.56 | 56.86 | 39.00 | 1.46 |
| penthiopyrad + Cmpd. I | 1.56 + 0.39 | 50.98 | 39.00 | 1.31 |
| trifloxystrobin + Cmpd. I | 6.25 + 1.56 | 99.61 | 90.00 | 1.11 |
| trifloxystrobin + Cmpd. I | 6.25 + 0.39 | 99.61 | 90.00 | 1.11 |
| trifloxystrobin + Cmpd. I | 6.25 + 0.10 | 99.61 | 90.00 | 1.11 |
| trifloxystrobin + Cmpd. I | 6.25 + 0.03 | 99.61 | 90.00 | 1.11 |
| trifloxystrobin + Cmpd. I | 6.25 + 0.01 | 100.00 | 90.00 | 1.11 |
| trifloxystrobin + Cmpd. I | 1.56 + 1.56 | 100.00 | 55.00 | 1.82 |
| trifloxystrobin + Cmpd. I | 1.56 + 0.39 | 100.00 | 55.00 | 1.82 |
| trifloxystrobin + Cmpd. I | 1.56 + 0.10 | 99.22 | 55.00 | 1.80 |
| trifloxystrobin + Cmpd. I | 1.56 + 0.03 | 99.22 | 55.00 | 1.80 |
| trifloxystrobin + Cmpd. I | 1.56 + 0.01 | 100.00 | 55.00 | 1.82 |
| fluoxastrobin + Cmpd. I | 1.56 + 1.56 | 99.61 | 41.00 | 2.43 |
| fluoxastrobin + Cmpd. I | 1.56 + 0.39 | 100.00 | 41.00 | 2.44 |
| fluoxastrobin + Cmpd. I | 1.56 + 0.10 | 99.61 | 41.00 | 2.43 |
| fluoxastrobin + Cmpd. I | 1.56 + 0.03 | 98.82 | 41.00 | 2.41 |
| fluoxastrobin + Cmpd. I | 1.56 + 0.01 | 99.61 | 41.00 | 2.43 |
| fluoxastrobin + Cmpd. I | 0.39 + 1.56 | 98.82 | 31.00 | 3.19 |
| fluoxastrobin + Cmpd. I | 0.39 + 0.39 | 90.59 | 31.00 | 2.92 |
| fluoxastrobin + Cmpd. I | 0.39 + 0.10 | 65.88 | 31.00 | 2.13 |
| fluoxastrobin + Cmpd. I | 0.39 + 0.03 | 62.75 | 31.00 | 2.02 |
| fluoxastrobin + Cmpd. I | 0.39 + 0.01 | 64.71 | 31.00 | 2.09 |
| benzovindiflupyr + Cmpd. I | 0.39 + 1.56 | 100.00 | 67.00 | 1.49 |
| benzovindiflupyr + Cmpd. I | 0.39 + 0.39 | 98.82 | 67.00 | 1.47 |

TABLE 1-continued

Synergistic Interactions Of Compound I And Other Fungicides In 1 Day Protectant (1 DP) *Puccinia recondita* (PUCCRT) Tests.

| Composition | Rates (ppm)* | PUCCRT* (% DC)* Observed* | PUCCRT* (% DC)* Expected* | Synergism Factor* |
|---|---|---|---|---|
| benzovindiflupyr + Cmpd. I | 0.39 + 0.10 | 99.22 | 67.00 | 1.48 |
| benzovindiflupyr + Cmpd. I | 0.39 + 0.03 | 99.61 | 67.00 | 1.49 |
| benzovindiflupyr + Cmpd. I | 0.39 + 0.01 | 97.65 | 67.00 | 1.46 |
| benzovindiflupyr + Cmpd. I | 0.10 + 1.56 | 68.63 | 37.00 | 1.85 |

*PUCCRT = Wheat Brown Rust; *Puccinia recondita*
*% DC Observed = Percent disease control observed
*% DC Expected = Percent disease control expected
*ppm = Parts per million
*Synergism factor = (% DC Observed/% DC Expected); Values > 1.0 are synergistic.

TABLE 2

Synergistic Interactions Of Compound I And Other Fungicides In 3 Day Curative (3 DC) *Puccinia recondita* (PUCCRT) Tests.

| Composition | Rates (ppm)* | PUCCRT* (% DC)* Observed* | PUCCRT* (% DC)* Expected* | Synergism Factor* |
|---|---|---|---|---|
| penthiopyrad + Cmpd. I | 1.56 + 1.56 | 66.67 | 14.00 | 4.76 |
| penthiopyrad + Cmpd. I | 1.56 + 0.39 | 43.14 | 14.00 | 3.08 |
| penthiopyrad + Cmpd. I | 1.56 + 0.03 | 23.53 | 14.00 | 1.68 |
| picoxystrobin + Cmpd. I | 6.25 + 1.56 | 74.51 | 53.00 | 1.41 |
| picoxystrobin + Cmpd. I | 6.25 + 0.39 | 64.71 | 53.00 | 1.22 |
| picoxystrobin + Cmpd. I | 6.25 + 0.03 | 62.75 | 53.00 | 1.18 |
| fluoxastrobin + Cmpd. I | 1.56 + 1.56 | 87.06 | 73.00 | 1.19 |
| fluoxastrobin + Cmpd. I | 1.56 + 0.39 | 90.20 | 73.00 | 1.24 |
| fluoxastrobin + Cmpd. I | 1.56 + 0.10 | 89.02 | 73.00 | 1.22 |
| fluoxastrobin + Cmpd. I | 1.56 + 0.03 | 90.98 | 73.00 | 1.25 |
| benzovindiflupyr + Cmpd. I | 6.25 + 1.56 | 90.20 | 73.00 | 1.24 |
| benzovindiflupyr + Cmpd. I | 6.25 + 0.39 | 82.35 | 73.00 | 1.13 |

*PUCCRT = Wheat Brown Rust; *Puccinia recondita*
*% DC Observed = Percent disease control observed
*% DC Expected = Percent disease control expected
*ppm = Parts per million
*Synergism factor = (% DC Observed/% DC Expected); Values > 1.0 are synergistic.

What is claimed:

1. A synergistic fungicidal mixture, comprising:
a fungicidally effective amount of a compound of Formula I:

Formula I and
at least one fungicide selected from the group consisting of fluoxastrobin, trifloxystrobin, and picoxystrobin, wherein a concentration ratio of the compound of Formula I to the at least one fungicide is from about 1:625 to about 1:5.

2. The mixture of claim 1, wherein the fungicide is fluoxastrobin and the concentration ratio of the compound of Formula I to fluoxastrobin is from about 1:156 to about 1:5.

3. The mixture of claim 1, wherein the fungicide is trifloxystrobin and the concentration ratio of the compound of Formula I to trifloxystrobin is from about 1:625 to about 1:5.

4. The mixture of claim 1, wherein the fungicide is picoxystrobin and the concentration ratio of the compound of Formula I to picoxystrobin is from about 1:208 to about 1:5.

5. A fungicidal composition comprising a fungicidally effective amount of the fungicidal mixture of claim 1 and an agriculturally acceptable adjuvant or carrier.

6. The mixture of claim 1, wherein the concentration ratio of the compound of Formula I to the at least one fungicide is from about 1:17 to about 1:625.

7. The synergistic fungicidal mixture of claim 1, wherein the mixture has a synergism factor against *Puccinia recondite* of 1.11 or greater in a 1 day protectant test of Yuma wheat seedlings, wherein the Yuma wheat seedlings were exposed to 100% relative humidity for 24 hours after inoculation with the *Puccinia recondite*.

8. The synergistic fungicidal mixture of claim 1, wherein the mixture has a synergism factor against *Puccinia recondite* of 1.11 or greater in a 3 day curative test of Yuma wheat seedlings, wherein the Yuma wheat seedlings were exposed to 100% relative humidity for 24 hours after inoculation with the *Puccinia recondite*.

9. The mixture of claim 1, wherein the concentration ratio of the compound of Formula I to the at least one fungicide is from about 1:5 to about 1:52.

10. A method for reducing or controlling a fungal attack on a plant, the method comprising: applying a fungicidally effective amount of a compound of Formula I:

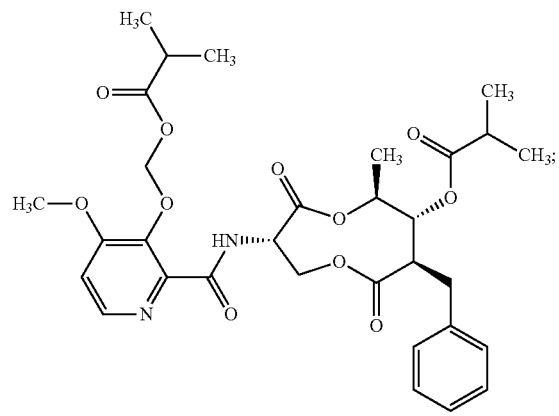

Formula I and
at least one fungicide selected from the group consisting of fluoxastrobin, trifloxystrobin, picoxystrobin, and benzovindiflupyr, wherein a concentration ratio of the compound of Formula I to the at least one fungicide is from about 1:625 to about 1:5;
wherein said effective amount is applied to at least one of the plant, an area adjacent to the plant, soil adapted to support growth of the plant, a root of the plant, foliage of the plant, and a seed adapted to produce the plant.

11. The method of claim 10, wherein the fungicide is fluoxastrobin and the concentration ratio of the compound of Formula I to fluoxastrobin is from about 1:156 to about 1:5.

12. The method of claim 10, wherein the effective amount is applied at a rate between 110 g/ha and 500 g/ha.

13. The method of claim 10, wherein the fungicide is trifloxystrobin and the concentration ratio of the compound of Formula I to trifloxystrobin is from about 1:625 to about 1:5.

14. The method of claim 10, wherein the fungicide is picoxystrobin and the concentration ratio of the compound of Formula I to picoxystrobin is from about 1:208 to about 1:5.

15. The method of claim 10, wherein the plant is infected with *Puccinia recondite*.

16. A method for reducing or controlling a fungal attack on a plant, the method comprising: applying a fungicidally effective amount of a compound of Formula I:

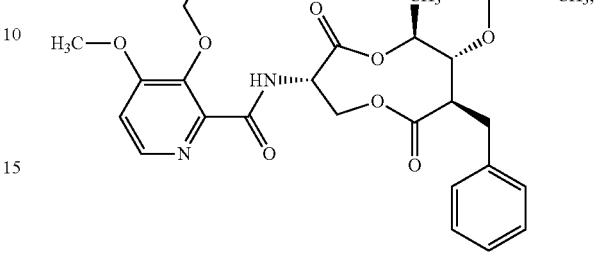

Formula I and
at least one fungicide selected from the group consisting of fluoxastrobin, trifloxystrobin, picoxystrobin, and benzovindiflupyr, wherein a concentration ratio of the compound of Formula I to the at least one fungicide is from about 1:625 to about 1:5;
wherein said effective amount is applied to at least one of the plant, an area adjacent to the plant, soil adapted to support growth of the plant, a root of the plant, foliage of the plant, and a seed adapted to produce the plant.

17. A synergistic fungicidal mixture, comprising:
a fungicidally effective amount of a compound of Formula I:

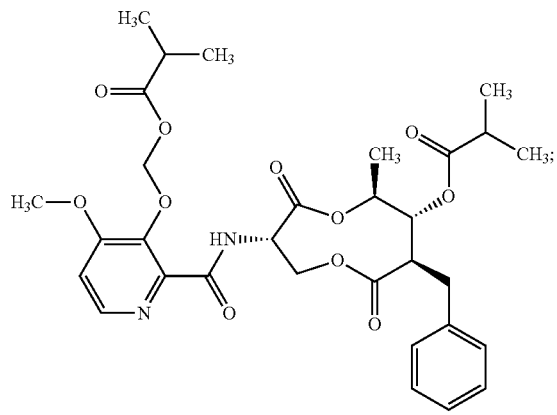

Formula I and
benzovindiflupyr, wherein a concentration ratio of the compound of Formula I to benzovindiflupyr is from about 4:1 to about 1:39.

18. The mixture of claim 17, wherein the concentration ratio of Formula I to benzovindiflupyr is from about 1:4 to about 1:13.

* * * * *